*United States Patent* [19]

Sucholeiki et al.

[11] Patent Number: 5,834,121

[45] Date of Patent: Nov. 10, 1998

[54] COMPOSITE MAGNETIC BEADS

[75] Inventors: Irving Sucholeiki, Watertown, Mass.; Graham Margetts; Mark Roberts, both of Shrewsbury, United Kingdom

[73] Assignees: Solid Phase Sciences Corp., Watertown, Mass.; Polymer Laboratories Ltd., Shropshire, United Kingdom

[21] Appl. No.: 585,905

[22] Filed: Jan. 16, 1996

[51] Int. Cl.⁶ .................................. B32B 5/16; B05D 7/00
[52] U.S. Cl. .................. 428/407; 427/221; 428/694 BA; 428/900
[58] Field of Search ..................................... 428/403, 407, 428/694 BA, 900; 427/215, 220, 221

[56] References Cited

U.S. PATENT DOCUMENTS

| | | | |
|---|---|---|---|
| 4,267,247 | 5/1981 | Ziolo et al. | 430/120 |
| 4,421,660 | 12/1983 | Sole nee Hajna | 252/62.54 |
| 4,554,088 | 11/1985 | Whitehead et al. | 252/62.54 |
| 4,654,267 | 3/1987 | Ugelstad et al. | 428/407 |
| 4,774,265 | 9/1988 | Ugelstad et al. | 521/55 |
| 5,091,206 | 2/1992 | Wang et al. | 427/2 |
| 5,108,636 | 4/1992 | Leising et al. | 252/62.54 |
| 5,147,722 | 9/1992 | Koslow | 428/402 |
| 5,169,754 | 12/1992 | Siiman et al. | 435/5 |
| 5,232,782 | 8/1993 | Charmot | 428/405 |
| 5,277,979 | 1/1994 | Kielbania et al. | 428/402.21 |
| 5,283,079 | 2/1994 | Wang et al. | 427/2 |
| 5,356,713 | 10/1994 | Charmot et al. | 428/407 |
| 5,395,688 | 3/1995 | Wang et al. | 428/327 |
| 5,583,056 | 12/1996 | Brouwer | 436/525 |
| 5,639,620 | 6/1997 | Siiman et al. | 435/7.21 |

OTHER PUBLICATIONS

Szymonifka et al *Tetrahedon Letters* vol. 36. #10 pp. 1597–1600 1995.

*Primary Examiner*—H. Thi Le
*Attorney, Agent, or Firm*—Sharon L. Day; Jacob N. Erlich; Jerry Cohen

[57] ABSTRACT

This invention provides a novel composite magnetic bead and a method for making the composite magnetic bead. The composite magnetic bead is comprised of a matrix formed from vinyl monomers throughout which is distributed primary beads, each primary bead of which is a magnetizable metal oxide encapsulated in a rigid polymeric coating. The matrix structure allows the composite magnetic bead to swell in organic solvents without loss of the intermeshed primary beads. Further, the matrix can be functionalized to allow the covalent bonding of sites useful for organic syntheses.

The composite magnetic beads are made utilizing a core-shell polymerization techinque under conditions which preserve the oxidation state of the magnetizable metal oxide in the primary particles. In one embodiment, primary beads, each having a hydrophobic exterior surface, are dispersed in an inert solvent with a vinyl monomer and a crosslinking agent for that monomer to form a dispersed phase. The dispersed phase is mixed into an aqueous solvent-dispersing agent phase and stirred until the desired droplet size is achieved, then polymerization is initiated. After removal of the solvent and unreacted components, the composite magnetic beads are dried and sieved.

29 Claims, 2 Drawing Sheets

5,834,121

COMPOSITE MAGNETIC BEADS

I. FIELD OF THE INVENTION

The present invention relates to a solid phase polymeric support system which can be suspended in a solvent and which can be recovered magnetically. More specifically, a paramagnetic bead useful for biomedical and industrial applications is provided.

II. BACKGROUND OF THE INVENTION

Solid phase support systems which can be suspended in solution and subsequently recovered have a wide variety of uses medically and in separation science. Assays both biological and chemical frequently require the separation of one specific component from another. For example, immunoassays require separation of bound components from free. When chemical syntheses are performed, products and reactants must be separated. Additionally, solid phase support systems can be used medically, for example for localized drug delivery. While some similarities in the requirements for the separation support system needed for various purposes exist, specifications also vary according to the use.

Particles or beads having inducible magnetic properties have been suggested for use as separation support system, especially where the medium in which the separation performed is aqueous. This type of separation support system utilizes small particles of transition metals such as iron, nickel, copper, cobalt and manganese to form metal oxides which can be caused to have inducible magnetic properties in the presence of magnets which are transitory; such particles are termed paramagnetic or superparamagnetic. To form paramagnetic or superparamagnetic beads, metal oxides have been coated with polymers which are relatively stable in water. For example, U.S. Pat. No. 4,554,088 (Whitehead, et al.) discloses paramagnetic particles comprising a metal oxide core surrounded by a coat of polymeric silane; U.S. Pat. No. 5,356,713 (Charmot), discloses a magnetizable microsphere comprised of a core of magnetizable particles surrounded by a shell of a hydrophobic vinylaromatic monomer; U.S. Pat. No. 5,395,688 (Wang) discloses a polymer core which has been coated with a mixed paramagnetic metal oxide-polymer layer, the disclosure of each incorporated herein by reference. Another method utilizes a polymer core to adsorb metal oxide such as for example in U.S. Pat. No. 4,774,265 (Ugelstad), incorporated herein by reference.

Magnetically separable support systems have been suggested for use in organic or biochemical syntheses (Sucholeiki, U.S. patent application Ser. No. 08/462,201), incorporated herein by reference. Small organic molecules may be synthesized by affixing a first reactant to a magnetizable bead, then sequentially adding a solution containing the next reactant, allowing the reaction to occur, and separating the product from the added reactant. By varying the type and sequence of reactants added, whole libraries of products with known compositions can be generated rapidly. This type of approach is especially useful for medicinal chemistry and drug discovery, *Tetrahedron Letters,* 36:1597 (1995), incorporated herein by reference. A similar approach to DNA, RNA, and polypeptide synthesis is shown in EP 113 452 (Benner), incorporated herein by reference.

When magnetically separable support systems are used for combinatorial chemistry, the demands on the system's stability increase as does the desired density of sites for binding. Further, the chemistry of the binding site changes. For example, in drug discovery related syntheses where the demand for a large output of chemically diverse small molecules is very high, the support system may be required to withstand high temperatures and harsh polar solvents while maintaining its magnetic properties. It is important in this application that the particles or beads can be easily and reliably recovered because the beads are repeatedly pooled magnetically then resuspended. Most importantly, a high density of available reaction sites is desired. Unlike immunoassays, covalent binding of the reactants to the support generally is required.

Known magnetically separable beads have several shortcomings as a support system, especially where an organic solvent is used for chemical syntheses. The number of binding sites per bead is less than desired. The beads tend to fail magnetically with use, frequently because the outer coating stability is insufficient. The availability of a binding site on any individual bead is not constant. Sites may be "buried" or become lost, because the beads tend to swell or contract or dissolve depending upon the solvent and temperature conditions. In EP 113 452, it is taught that beads that swell lose their metal oxide particles into the solution.

Surprisingly, the novel bead of this invention provides a support system which retains its magnetic properties, has a high loading capacity, and maintains availability of reaction sites, even though it swells and contracts depending upon the solvent and temperature conditions to which it is exposed.

III. SUMMARY OF THE INVENTION

The present invention provides a novel composite magnetic bead and a method for making such a bead. The invention finds use as a separation support system that can be suspended in solution, then collected by applying a magnetic force, and subsequently resuspended. Such a separation support system is useful for a wide range of biomedical, biochemical and industrial applications involving a variety of materials, from macro-separation procedures such as separating oil from water after an oil spill to micro-separations such as used in immunological assays and in organic chemical syntheses. These beads are especially useful as supports for chemical synthesis where rapid separation of products from reactants in solution is desired.

The novel composite bead comprises 1) a plurality of primary beads or particles, each of which is a polymer-coated or polymer-encapsulated metal oxide that has inducible magnetic properties, and 2) a mesh or matrix comprising of a thermoplastic polymer resin that is microporous, and which is capable of swelling or expanding in organic solvent, wherein the primary beads are randomly distributed throughout the matrix. The composite bead is essentially spherical in shape and has an uneven, undulating surface.

The primary bead is comprised of at least one metal oxide particle encapsulated in a rigid polymeric coating. The metal oxide particle or magnetite that is encapsulated may be obtained by known methods. The rigid, polymeric coating that forms the encapsulating layer surrounding the metal oxide particle must be solvent-stable such that the metal oxide particle(s) is retained within the coating under harsh conditions of temperature and solvent. The encapsulated metal oxide particle must be capable of participating in a core-shell polymerization to form the composite bead. Further, the rigid polymeric coating should render the primary bead either hydrophilic or hydrophobic. It is especially preferred that the coated magnetite particle be hydrophobic or be capable of being rendered hydrophobic.

To form the composite bead, the encapsulated metal oxide particle or primary bead is then enmeshed in a microporous matrix formed from a low cross-linked thermoplastic polymer. The matrix polymer is formed from one or more monomers. Some of the monomers may have reactive side groups. Preferably, the monomers used to form the microporous polymeric matrix are vinyl monomers. The resultant composite bead is spherical in shape with an uneven, undulating surface and has primary beads distributed throughout the matrix.

The novel composite beads of the present invention may be made by a number of different polymerization methods. The preferred method involves a suspension polymerization procedure involving a core-shell polymerization of a mesh-forming cross-linkable monomer composition and a polymer in the shell or capsule surrounding the metal oxide core. A dispersing agent which may act as a stabilizer as well as a dispersant is added to an aqueous solution to form a continuous fluid phase. Conditions that result in a strongly acidic environment are to be avoided. In a preferred embodiment wherein styrene monomers and derivatives of styrene monomers are utilized for forming the matrix, an antioxidant that also acts to inhibit emulsion formation preferably is added to the dispersed phase.

The novel composite bead is able to swell and contract depending upon the solvent to which it is exposed while maintaining both paramagnetic or superparamagnetic properties and a high loading capacity.

IV. BRIEF DESCRIPTION OF THE DRAWINGS

V. DETAILED DESCRIPTION OF THE INVENTION

A novel composite magnetic bead of the present invention comprises a plurality of encapsulated metal oxide particles, and a microporous polymer resin matrix that has the capacity for functionalization or derivatization. The encapsulated metal oxide particles, herein also referred to as primary beads, have a rigid polymeric coating encapsulating the metal oxide particle. The composite magnetic beads swell in organic solvents such as dimethylformamide and dimethyl sulfoxide without losing their paramagnetic properties and provide a high surface area that can contact the solvent and which can be functionalized to allow binding to the polymeric surface, thereby providing increased capacity for organic synthesis and increased loading capacity for separating a bound component from a component in solution or suspension. These composite magnetic beads are able to withstand high temperatures in highly polar solvents as well as high energy sonication.

As used herein the term "metal oxide particle" refers to any oxide of a metal or metal alloy having paramagnetic or superparamagnetic properties. "Paramagnetic particle" is defined as a metal oxide particle which is susceptible to the application of external magnetic fields, yet is unable to maintain a permanent magnetic domain. The term "rigid" refers to a polymeric coating that cross linked to the extent that the polymeric coating stabilizes the metal oxide particle within the coating (i.e. the coating essentially does not swell or dissolve) so that the particle remains enclosed therein. The term "microporous" refers to a resinous polymeric matrix that swells or expands in polar organic solvent. The term "load" is used to mean the capacity of the bead for attachment sites useful for functionalization or derivatization.

Figure 1:
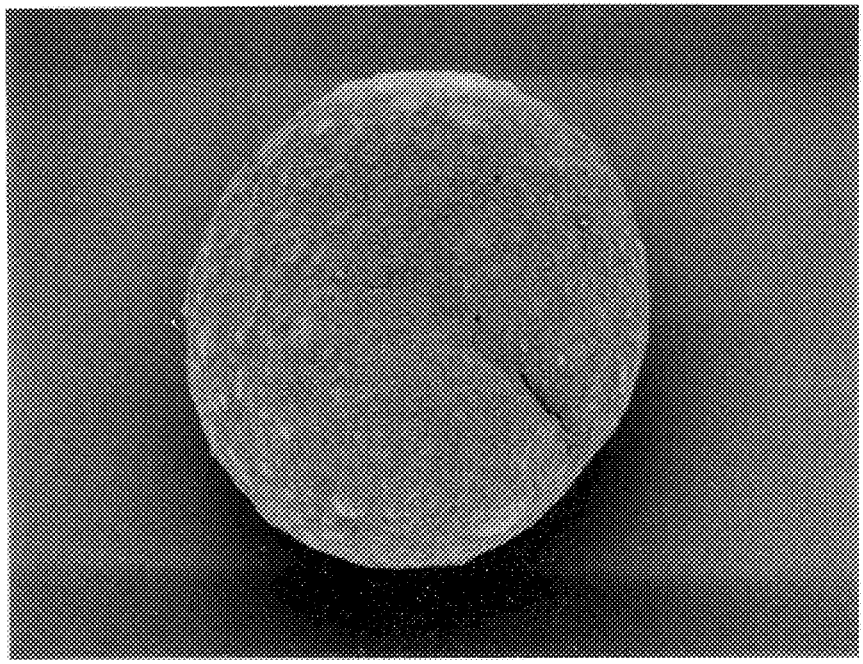
FIG. 1 is a scanning electron micrograph of a composite magnetic bead at a magnification of 150×.
Figure 2:
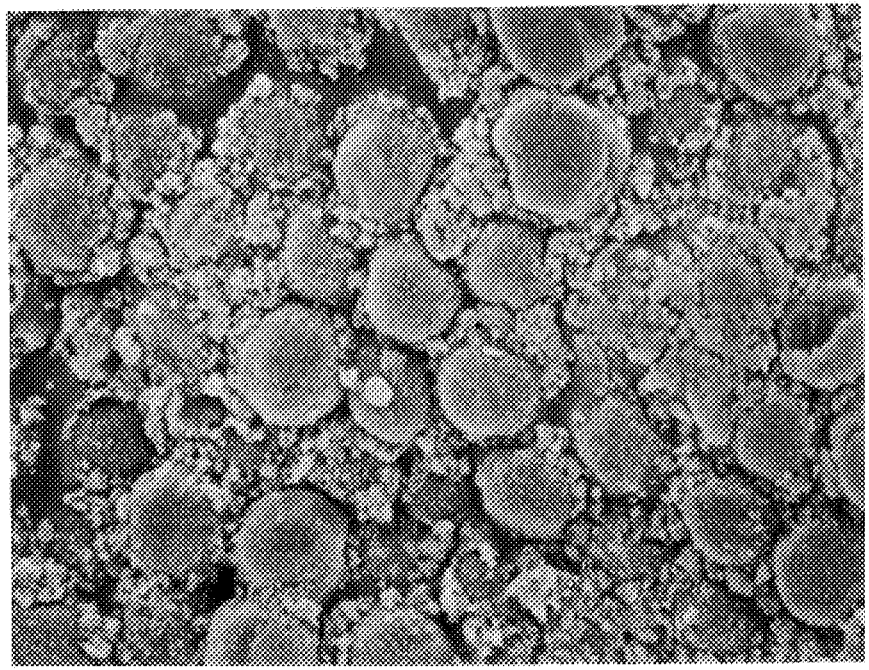
FIG. 2 is a scanning electron micrograph of the surface of a composite magnetic bead at a magnification of 6500×.
Figure 3:
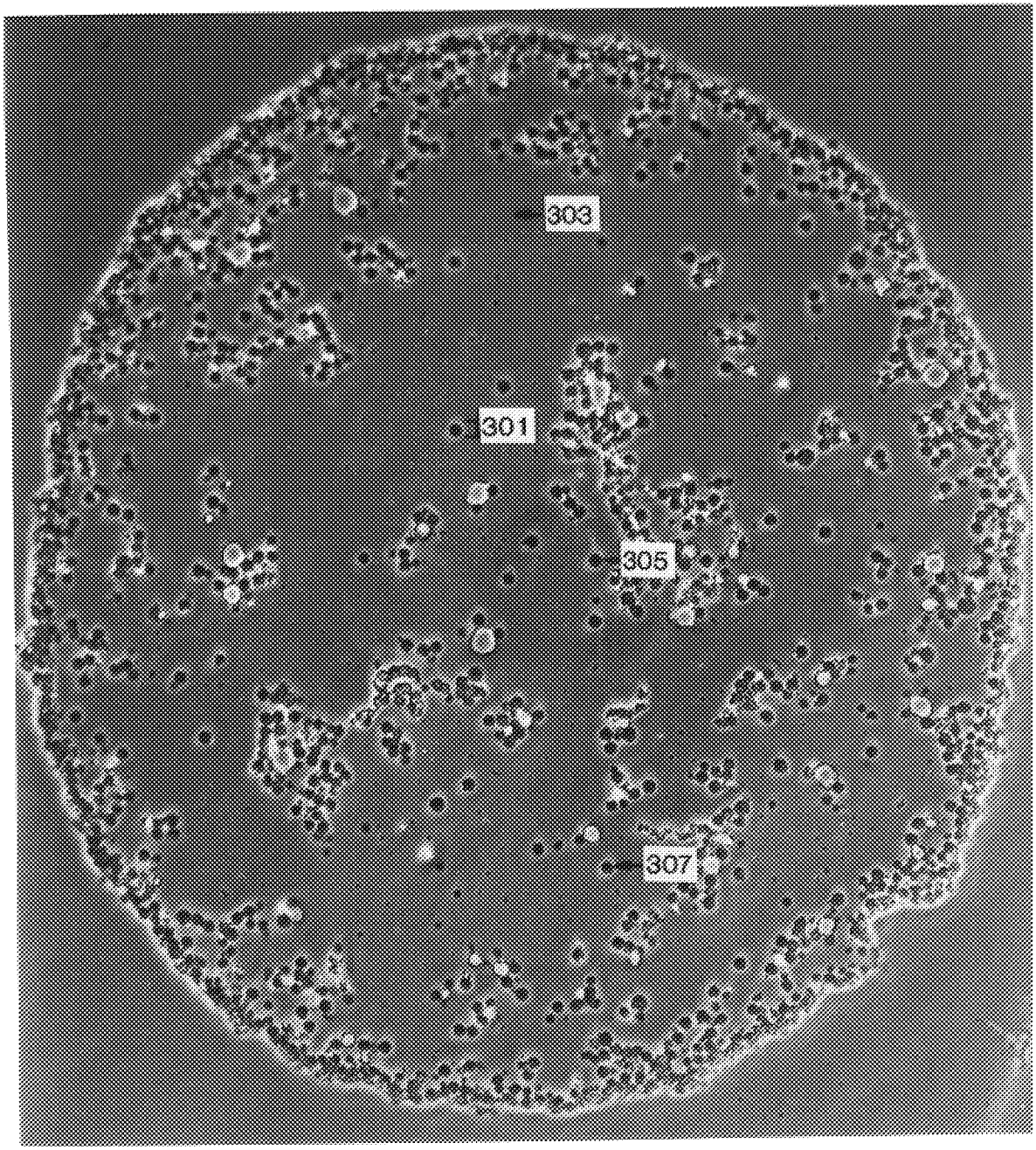
FIG. 3 is a phase contrast light micrograph of a cross-section of a composite magnetic bead at a magnification of 560× which illustrates the distribution of a plurality of metal oxide particles, each having a rigid polymeric coating, throughout a microporous matrix.

A novel composite magnetic bead or particle of this invention is shown in the scanning electron micrograph, FIG. 1. In FIG. 2, the surface of a composite magnetic bead such as seen in FIG. 1 is shown. Primary beads (201) comprising a magnetite particle and a rigid polymeric coating can be seen as discrete protrusions intermeshed in areas of microporous polymeric resin (203). Distribution of the primary beads throughout the composite magnetic bead is illustrated in FIG. 3, a phase contrast light micrograph of a cross-section of a composite bead. The primary beads are seen as rounded, dark images (301) at the edge of the composite bead, and throughout the interior of the composite bead cross-section. The darkened center (305) of each primary bead is believed to be the metal oxide. The shadow or halo (307) surrounding each magnetite particle is believed to be the rigid polymeric coating. The primary beads are themselves enmeshed or enclosed in a resinous polymer (303) which forms a network or matrix of low cross-linked polymer among the primary beads.

The primary beads or particles of this invention may be prepared from the raw materials or from metal oxides that are encapsulated by monomers which when crosslinked form rigid, polymeric coatings. Suitable substances which may be incorporated as magnetizable materials, for example, include iron oxides such as magnetite, ferrites of manganese, cobalt, and nickel, hematite and various alloys. Magnetite is the preferred metal oxide. Frequently, metal salts are taught to be converted to metal oxides then either coated with a polymer or adsorbed into a bead comprising a thermoplastic polymer resin having reducing groups thereon. When starting with metal oxide particles to obtain a hydrophobic primary bead, it is necessary to provide a rigid coating of a thermoplastic polymer derived from vinyl monomers, preferably a cross-linked polystyrene that is capable of binding or being bound by a microporous matrix. Magnetic particles may be formed by procedures shown in Vandenberge, et al., "Preparation and Magnetic Properties of Ultrafine Cobalt Ferrites," *J. of Magnetism and Magnetic Materials,* 15–18: 1117–18 (1980); E. Matijevic, "Monodispersed Metal (Hydrous) Oxides—A Fascinating Field of Colloidal Science," *Acc. Chem. Res.,* 14:22–29 (1981), U.S. Pat. Nos. 5,091,206; 4,774,265; 4,554,088; and 4,421,660. Examples of primary beads that may be used in this invention are shown in U.S. Pat. Nos. 5,395,688; 5,318,797; 5,283,079; 5,232,7892; 5,091,206; 4,965,007; 4,774,265; 4,654,267; 4,490,436; 4,336,173; and 4,421,660, each disclosure of which is incorporated herein by reference. Or, primary beads may be obtained commercially from available hydrophobic or hydrophilic beads that meet the starting requirements of size, sufficient stability of the polymeric coating to swelling in solvents to retain the paramagnetic particle, and ability to adsorb or absorb the vinyl monomer used to form the enmeshing matrix network. Preferably, the primary bead is a hydrophobic, polystyrene encapsulated, paramagnetic bead. Such polystyrene paramagnetic beads are available from Dynal, Inc. (Lake Success, N.Y.), Rhone Poulonc (France), and SINTEF (Trondheim, Norway). The use of toner particles or of magnetic particles having a first coating of an unstable polymer which are further encapsulated to produce an exterior rigid polymeric coating is also contemplated.

Primary particles or beads have an average diameter of about 100 micrometers or less, preferably 1 to 10 micrometers. The primary particles or beads must be capable of participating in a polymerization reaction, preferably as seed particles, with additional monomers which form a microporous thermoplastic polymer mesh or matrix. The rigid polymer coat enclosing the metal oxide must be of a thickness, density, and composition such that it retains the metal oxide therein during and after the polymerization resulting in the final composite bead. An example of one type of rigid polymeric coating is a polystyrene coating formed from a styrene composition having at least a 10% by monomer weight content of divinyl benzene. Further, the coating must not negatively affect the magnetic properties of the enclosed magnetite. The rigid polymeric coating may render the primary particle hydrophobic or hydrophilic. Preferably, the primary beads are hydrophobic due to the properties of the rigid polymeric coating. The encapsulating rigid polymer may be obtained from monomers or combinations of monomers such as a polystyrene, a poly (chloromethyl styrene), a poly(bromo styrene), a poly (methyl methacrylate), or a poly(methyl acrylate). It should be apparent to those skilled in the art that the required coating thickness and the required degree of monomer cross-linking are dependent and thus can be varied relative to one another to achieve the desired result.

Polymerization of the matrix to enmesh the primary beads thus forming the composite beads, occurs in a two phase system, a continuous fluid phase and a dispersed phase, using a method similar to that described in U.S. Pat. No. 5,277,979 (Kielbania, et. al.), the disclosure of which is incorporated herein by reference. The primary beads may be hydrophilic or hydrophobic. When the primary beads are hydrophobic, then the continuous fluid phase is hydrophilic and the dispersed phase is hydrophobic. An aqueous solvent such as water is combined with a dispersant which may also act as an emulsion stabilizer to form the continuous fluid phase. The primary beads and matrix forming monomers are combined in the dispersed phase. Primary beads sized from about 0.05 to about 50.00 um, preferably from about 1 to about 10 um, are used.

The monomers that are suitable for forming the matrix are vinyl monomers such as styrenes, acrylates, methacrylates and the like. Derivatives of these vinyl monomers, for example, methyl acrylate, butyl acrylate, methyl methacrylate, and functionalized derivatives, for example, bromo styrene, chloromethyl styrene, 2-aminoethyl methacrylate, and trimethylammoniumethyl methacrylate, may also be used. Inclusion of a desired percentage of functionalized derivatives eliminates the step of providing functionalized groups after the polymerization has been completed. When the monomer chosen to be added in the dispersed phase has only one vinyl group, it is desirable to include another monomer having more than one vinyl group to facilitate cross-linking. The ratio of various monomers is chosen to provide a final microporous polymer which is cross-linked to the extent of about 1 to 8%.

A polymerization initiator may also be added at about 0.5 to 10% by weight based upon the weight of the total monomer(s) added when the polymeric matrix is formed using a free radical polymerization. The preferred initiators are alkyl and aryl peroxides such as dioctanoyl peroxide and benzoyl peroxide, and nitrites such as azobisisobutyronitrile. Preferably, benzoyl peroxide is used. However, other means of polymerization such as redox or uv irradiation could also be used and at least in the case of UV polymerization, the polymerization initiator could be eliminated or a photoinitiator may be used.

The dispersing agent is preferably added to aid in setting the final composite bead size. Examples of dispersing agents include polymeric dispersants and protective colloids; however, surfactants may also function in this manner. Dispersants include gum arabic, gelatin, cellulose-based compounds, maleic-anhydride-styrene copolymers, and partially hydrolyzed polyvinyl alcohol. Suitable surfactants include sodium lauryl sulfate, sodium dodecylbenzene sulfonate, and dialkyl succinates. The dispersant is present in an amount of from about 0.1 to about 10 wt. % based upon the weight of the continuous phase solvent.

The diluent is an inert solvent in the matrix-forming monomers can be solublized. When the primary bead has a hydrophobic encapsulating coat, the diluent preferably is oil-soluble. Examples of preferred diluents useful when the primary bead is hydrophobic and the monomers are selected from the group of styrene monomers include diethylbenzene, toluene, and dichloroethane. The diluent is used at a concentration of up to 150 wt. % based upon the weight of monomer to be polymerized. The diluent chosen may slightly swell the polymeric coating on the primary bead so long as the coating maintains the metal oxide therein.

In a preferred embodiment, styrene monomers, divinyl benzene monomers at about 1 to about 8 weight % of the total monomers, a diluent or solvent for the monomers and hydrophobic primary beads at a weight ratio percent of about 1 to 20%, preferably about 2 to 10% based upon the total weight amount of the monomer(s) added for the polymerization, are combined with a polymerization initiator and an emulsion inhibitor to form the dispersed phase. A continuous fluid phase is formed from purified water and partially hydrolyzed polyvinyl alcohol. A free radical polymerization is initiated when the continuous phase and the dispersed have been thoroughly mixed. A preferred emulsion inhibitor that also may act as an anti-oxidant is sodium nitrite. It should be noted that when methacrylate based monomers are combined to form the polymeric matrix, the addition of an emulsion inhibitor is unnecessary.

The dispersed phase is added to the continuous fluid phase in a ratio of about 1:20 to about 1:2, dispersed to continuous phase (vol:vol) and preferably at a ratio of about 1:10 to about 1:5. The continuous fluid phase-dispersed phase is vigorously mixed in an inert atmosphere for a time, at a temperature, and at a speed adapted to achieve the desired final composite bead size. The final beads are sieved and dried. The final bead size ranges from about 25 to 800 um. Beads in size ranges of 75 to 150 um and from 150 to 300 um are preferred. Typically, the ratio of the diameter of the primary bead to that of the composite bead ranges from about 1:2.5 to 1:800; most typically the range is 1:75 to 1:200.

Functional groups may be added to the final composite magnetic bead through further derivatization such as by the addition of amine groups using procedures taught by Merrifield et al., *Anal. Biochem.*, 117:147 (198 1).

The following examples are given to illustrate the invention and should not be construed as limiting its scope.

VI. EXAMPLES

Example 1

Preparation of High Load Paramagnetic Composite Beads

A continuous fluid phase is formed from water and polyvinyl alcohol. 600 grams of deionized water are weighed into a 1 Liter, 3 necked round-bottom flask fitted with a condenser, nitrogen inlet and an overhead stirrer (IKA). The flask is immersed in a water bath and the bath temperature set to 90° C. The water in the flask is purged with nitrogen from an air stone for 30 minutes. 6 grams of polyvinyl alcohol (Harco 26-88) (PVA) is added to the flask; the air stone is removed and a nitrogen blanket is maintained above the liquid surface for the duration of the reaction. The continuous fluid phase is stirred for 30 minutes at 90° C., then allowed to cool (with stirring) to 65° C. overnight. Separately, the dispersed phase is formulated from 0.15 grams of sodium nitrite ($NaNO_2$), 6 grams of primary hydrophobically coated paramagnetic beads, 70 grams of distilled styrene, 4.8 grams of divinyl benzene (63% divinyl content), 75 grams of diethyl benzene and 3 grams of benzoyl peroxide are mixed and degassed with nitrogen for 20 minutes. This mixture is poured into the continuous fluid phase, and the stirring speed adjusted to give droplets of the desired size (10–2000 micrometers). Reaction is allowed to proceed for 24 hours at 65° C. The reaction is then cooled, the particles are filtered. The product is washed with water to remove excess PVA and with tetrahydrofuran (THF) to remove unreacted monomer and inert diluents. The product was then dried and sieved.

Example 2

Preparation of High Load Chloromethyl Paramagnetic Particles 400 grams of deionized water is weighed into a 1 Liter, 3 necked round-bottom flask fitted with a condenser, nitrogen inlet and an overhead stirrer (IKA). The flask is immersed in a water bath and the bath temperature set to 90° C. The water in the flask is purged with nitrogen from an air stone for 30 minutes. 2 grams of polyvinyl alcohol (Harco 26-88) (PVA) is added to the flask. The air stone is removed and a nitrogen blanket is maintained above the liquid surface for the duration of the reaction. The PVA mixture is stirred for 30 minutes at 90° C., then allowed to cool (with stirring) to 65° C. overnight. Separately, 0.1 grams of sodium nitrite ($NaNO_2$), 6 grams of primary hydrophobically coated paramagnetic beads, 53.4 grams of distilled styrene, 2.5 grams of divinyl benzene (63% divinyl content), 65 grams of diethyl benzene, 10.4 grams of chloromethylstyrene and 1 grams of benzoyl peroxide are mixed and degassed with nitrogen for 20 minutes. This mixture is poured into the PVA solution, and the stirring speed adjusted to give droplets of the desired size (10–2000 micrometers). Reaction is allowed to proceed for 24 hours at 65° C. The reaction is then cooled, the particles filtered and the product washed with water to remove excess PVA and with tetrahydrofuran (THF) to remove unreacted monomer and inert diluents. The product is then dried and sieved. Elemental analysis gave 3.41 % chlorine (0.96 mmoles chlorine/gram of resin)

Example 3

Preparation of High Load Aminomethyl Paramagnetic Particles

To a 250 round bottom flask fitted with a condenser, nitrogen inlet and an overhead stirrer (IKA), was added 6 grams of chloromethyl paramagnetic beads prepared as in Example 2, 100 ml of dimethylformamide and 1.2 grams (6.4 mmole) potassium phthalimide and mixture stirred at 50° C. for 20 hours. At the end of 20 hours, the product was washed with dimethylformamide, methanol, water and ethanol and then dried under vacuum to provide phthalimide incorporated beads.

To 6 grams of phthalimide incorporated beads was added 200 ml of absolute ethanol and 2 ml of hydrazine monohydrate. The mixture was refluxed for 10 hours. The material was then filtered, washed with ethanol, aqueous sodium hydroxide, distilled water and ethanol in that order to give aminomethyl paramagnetic particles, dark black in color. Elemental analysis gave 2.01% nitrogen, 83.83% carbon, 7.10% hydrogen and 2.40% iron.

Example 4

Composite magnetic beads from the batch used to provide the micrograph of FIG. 1, were suspended in various solvents and the following was observed. Beads expand in dimethyl formamide (DMF), methylene chloride, and tetrahydrofuran. See Table 1.

When the composite beads are suspended in DMF and allowed to remain in the solvent for 1 hr at 100° C., then exposed to a neodynium magnetic separator such as is available from Advanced Magnetics Lab., Cambridge, Mass., the composite beads are seen to remain intact. Small rigid polymeric coated magnetite particles which have become separated from the microporous matrix are not observed.

TABLE 1

Volume Changes of Composite Paramagnetic Beads (100 mg) Having An Average Diameter of 400 micrometers

| Solvent | Volume (ml) | Change in Volume(ml) | Floats/Sinks |
|---|---|---|---|
| none (dry) | 0.7 | — | — |
| DMF | 1.6 | 0.9 | sinks |
| water | 0.7 | 0 | floats |

What is claimed is:

1. A composite magnetic bead comprising:
   a) microporous matrix of a first polymer, said first polymer comprising at least one vinyl monomer; and
   b) a plurality of primary beads, each primary bead comprising a metal oxide having inducible magnetic properties and a coating of a second polymer that comprises at least one vinyl monomer, said coating encapsulating said metal oxide, wherein said plurality of primary beads is distributed throughout said microporous matrix.

2. The composite magnetic bead of claim 1 wherein the diameter of said composite magnetic bead is at least twice the diameter of each of said primary beads.

3. The composite magnetic bead of claim 1 wherein said first polymer has a degree of cross-linking of between about 1 percent and about 8 percent.

4. The composite magnetic bead of claim 3 wherein the ratio of the diameter of said primary bead to the diameter of said composite magnetic bead is at least about 1:25.

5. The composite magnetic bead of claim 4 wherein said second polymer has a degree of cross-linking of greater than about 10 percent.

6. The composite magnetic bead of claim 4 wherein the ratio of said diameter of said primary bead to said diameter of said composite magnetic bead is at least about 1:75.

7. The composite magnetic bead of claim 1 wherein said first polymer and said second polymer at least one vinyl monomers are selected from the group consisting of styrene, styrene derivatives, and divinyl benzene.

8. The composite magnetic bead of claim 7 wherein said first polymer has chloromethyl groups.

9. The composite magnetic beads of claim 1 wherein said plurality exceeds twenty of said primary beads per said composite magnetic bead.

10. The composite magnetic beads of claim 4 wherein said plurality exceeds fifty of said primary beads per said composite magnetic bead.

11. The composite magnetic bead of claim 9 wherein incorporation of said metal oxide is directly proportional to the number of said plurality of primary beads in said composite magnetic bead.

12. The composite magnetic bead of claim 1 wherein said composite magnetic bead has a dry volume and wherein said dry volume increases by at least 50% when said composite magnetic bead is submerged in an organic solvent.

13. The composite magnetic bead of claim 12 wherein said organic solvent is dimethylformamide.

14. The composite bead of claim 1 wherein said at least one vinyl monomer of said first polymer has at least one functional group.

15. The composite magnetic bead of claim 14 wherein said functional group is a chloromethyl group.

16. The composite magnetic bead of claim 14 wherein said functional group is an aminomethyl group.

17. The composite magnetic bead of claim 1 wherein said at least one vinyl monomer of said first polymer is selected from the group consisting of styrene, styrene derivatives, and divinyl benzene.

18. The composite magnetic head of claim 1 wherein said polymer renders said plurality of primary beads hydrophilic.

19. A method for making a composite magnetic bead having a plurality of primary beads randomly distributed throughout said composite magnetic bead, said method comprising the steps of:
   (1) preparing a continuous fluid phase comprising a solvent and a dispersing agent;
   (2) preparing a dispersed phase comprising:
      (a) said plurality of primary beads, where each of said primary beads comprises a metal oxide particle having inducible magnetic properties and of a rigid polymeric coating encapsulating said metal oxide particle;
      (b) at least one vinyl monomer selected from the group consisting of styrenes, methacrylates, acrylates, and derivatives thereof; and
      (c) an inert diluent;
   (3) mixing said dispersed phase with said continuous fluid phase to form an emulsion having a plurality of droplets, each droplet containing said primary beads, each droplet having a diameter greater than 10 microns;
   (4) adsorbing said vinyl monomer onto said rigid polymeric coating of each of said plurality of primary beads; and
   (5) polymerizing said vinyl monomer to provide a microporous polymeric matrix interlinking said primary beads.

20. The method of claim 19 wherein said rigid polymeric coating renders each of said primary beads hydrophobic.

21. The method of claim 20 wherein said dispersed phase further includes a polymerization initiator.

22. The method of claim 21 wherein said dispersed phase further includes an emulsion inhibitor.

23. The method of claim 22 wherein the emulsion inhibitor is sodium nitrite.

24. The method of claim 23 wherein said microporous polymeric matrix is provided with chloromethyl groups.

25. The method of claim 24 wherein said chloromethyl groups are converted to aminomethyl groups.

26. The method of claim 19 wherein said dispersant is polyvinyl alcohol.

27. The method of claim 19 wherein said rigid polymeric coating renders each of said primary beads hydrophilic.

28. A composite magnetic bead comprises a microporous matrix and of a plurality of primary beads, each primary bead having a cross-linked polymeric coating enclosing a metal oxide particle, said metal oxide particle having inducible magnetic properties, said plurality of primary beads randomly distributed throughout said microporous matrix, said composite magnetic bead prepared according to the process of:
   (1) mixing a dispersing agent with an aqueous solvent to form a continuous fluid phase;
   (2) dispersing at least one vinyl monomer, a crosslinking monomer for said vinyl monomer, an emulsion inhibitor, a polymerization initiator and said plurality of primary beads in an inert solvent to form a dispersed phase, wherein said coating on each of said plurality of primary beads is comprises a polymer having a degree of cross-linking of at least about 10 percent;
   (3) mixing said continuous fluid phase and said dispersed phase at a speed to form a plurality of droplets, each droplet containing said plurality of primary beads, said vinyl monomer, and said crosslinking monomer;
   (4) initiating a free radical polymerization to form a polymeric mesh, thereby interlinking in said mesh said plurality of primary beads in each of said droplets; and
   (5) removing said inert solvent and said aqueous solvent.

29. The composite magnetic bead of claim 28 wherein said at least one vinyl monomer of said first polymer has a functional group.

* * * * *